(12) United States Patent
Holley (10) Patent No.: US 11,700,935 B2
(45) Date of Patent: *Jul. 18, 2023

(54) PORTABLE DEVICE FOR DENTAL HYGIENE, STORAGE, AND HYGIENE METHOD

(71) Applicant: Doreen Holley, Hopewell, NJ (US)

(72) Inventor: Doreen Holley, Hopewell, NJ (US)

(*) Notice: Subject to any disclaimer, the term of this patent is extended or adjusted under 35 U.S.C. 154(b) by 324 days.

This patent is subject to a terminal disclaimer.

(21) Appl. No.: 17/070,189

(22) Filed: Oct. 14, 2020

(65) Prior Publication Data

US 2021/0085070 A1 Mar. 25, 2021

Related U.S. Application Data

(63) Continuation of application No. 15/967,937, filed on May 1, 2018, now Pat. No. 10,820,687.

(51) Int. Cl.
*A46B 17/06* (2006.01)
*A46B 15/00* (2006.01)
*A46B 17/04* (2006.01)
*A61L 2/10* (2006.01)
*A46B 9/04* (2006.01)

(52) U.S. Cl.
CPC .......... *A46B 17/065* (2013.01); *A46B 9/04* (2013.01); *A46B 15/00* (2013.01); *A46B 17/04* (2013.01); *A61L 2/10* (2013.01); *A61L 2202/17* (2013.01)

(58) Field of Classification Search
CPC ....... A46B 9/04; A46B 15/00; A46B 15/0061; A46B 15/0002; A46B 17/04; A46B 17/06; A46B 17/065; A46B 2200/1066; A47L 1/06; A47L 13/12; A61L 2/10; A61L 2/26; A61L 2202/17; A61L 2/08

See application file for complete search history.

(56) References Cited

U.S. PATENT DOCUMENTS

| 835,365 | A | * | 11/1906 | Morgan | A46B 5/0033 132/311 |
| 3,325,847 | A | * | 6/1967 | Meranto | A47K 1/09 15/184 |
| 3,353,898 | A | * | 11/1967 | Lamberti | A46B 11/0003 132/308 |
| 3,593,725 | A | | 7/1971 | Ortega et al. | |

(Continued)

FOREIGN PATENT DOCUMENTS

KR 200434651 * 12/2006

*Primary Examiner* — Robert J Scruggs
(74) *Attorney, Agent, or Firm* — Carter, DeLuca & Farrell LLP (57) ABSTRACT

A dental hygiene device includes a housing, a toothbrush, and a sanitizing device. The housing includes a chamber therein. The housing defines a mouth and an opening. The housing includes a first width adjacent the mouth and a second width spaced apart from the mouth. The second width is larger than the first width. The toothbrush is detachably securable with the mouth of the housing. The toothbrush includes a head portion including bristles, and an engaging portion. The toothbrush is reconfigurable with the housing between a first configuration, in which, the bristles are external of the housing, and a second configuration, in which, the bristles are disposed within the chamber. The sanitizing device includes a plurality of light emitting diodes to provide ultraviolet light within the chamber of the housing.

16 Claims, 7 Drawing Sheets

(56) References Cited

U.S. PATENT DOCUMENTS

| | | | |
|---|---|---|---|
| 3,763,869 A | 10/1973 | Sanders | |
| 4,906,851 A | 3/1990 | Beasley et al. | |
| 5,423,427 A * | 6/1995 | Brown | A46B 15/0071 |
| | | | 206/362.2 |
| 6,099,813 A * | 8/2000 | Gipson, II | A61L 2/18 |
| | | | D6/528 |
| 6,715,952 B1 | 4/2004 | Aiken et al. | |
| 6,753,537 B2 | 6/2004 | Woo | |
| 7,815,383 B2 | 10/2010 | Hall | |
| 8,074,319 B2 | 12/2011 | Huang | |
| 8,168,936 B2 * | 5/2012 | DeFlumere | H01J 43/246 |
| | | | 250/214 R |
| 8,168,963 B2 | 5/2012 | Ratcliffe | |
| 9,000,398 B2 * | 4/2015 | Nelson | A61L 2/10 |
| | | | 15/4 |
| 9,961,985 B2 | 5/2018 | Shigeno | |
| 10,820,687 B2 | 11/2020 | Holley | |
| 2009/0010826 A1 | 1/2009 | Shin | |
| 2015/0147727 A1 | 5/2015 | Kandemir | |

* cited by examiner

PORTABLE DEVICE FOR DENTAL HYGIENE, STORAGE, AND HYGIENE METHOD

CROSS-REFERENCE TO RELATED APPLICATIONS

This application is a continuation application of U.S. patent application Ser. No. 15/967,937, filed on May 1, 2018, the contents of which are incorporated by reference herein.

BACKGROUND

Technical Field

The present disclosure relates to oral care devices, and more particularly, to a portable dental hygiene device.

Background of Related Art

There are many known portable toothbrushes in existence. Toothbrushes, especially when wet, are a natural haven for bacterial growth. Therefore, there is a continuing need for a dental hygiene device that is portable and effective in sterilizing the toothbrush and other oral hygiene products.

SUMMARY

In accordance with an embodiment of the present disclosure, there is provided a dental hygiene device including a housing, a toothbrush, and a sanitizing device. The housing includes a chamber therein. The housing defines a mouth and an opening. The housing includes a first width adjacent the mouth and a second width spaced apart from the mouth. The second width is larger than the first width. The toothbrush is detachably securable with the mouth of the housing. The toothbrush includes a head portion including bristles, and an engaging portion. The toothbrush is reconfigurable with the housing between a first configuration, in which, the bristles are external of the housing, and a second configuration, in which, the bristles are disposed within the chamber. The sanitizing device includes a plurality of light emitting diodes configured to provide ultraviolet light within the chamber of the housing.

In an embodiment, the chamber may define a recess in registration with the bristles when the toothbrush is in the second configuration.

In another embodiment, when the toothbrush is in the second configuration, the bristles may be spaced apart from the recess.

In yet another embodiment, the sanitizing device may include a hook portion including the plurality of light emitting diodes.

In still yet another embodiment, the sanitizing device may include a USB port electrically coupled with the plurality of light emitting diodes.

In still yet another embodiment, the USB port may be in registration with the opening of the housing.

In still yet another embodiment, the housing may include a base portion and a cover hingedly coupled to the base portion.

In an embodiment, the base portion may include an outer surface defining a recess configured to receive an oral care material.

In another embodiment, the sanitizing device may be detachably coupled with the housing by a plurality of pins.

In yet another embodiment, the sanitizing device may be detachably secured with the opening of the housing.

In still yet another embodiment, the housing may include scalloped portions.

In another embodiment, the mouth may be adjacent the opening.

In yet another embodiment, the chamber may include a reflective surface.

In still yet another embodiment, the sanitizing device may at least partially surround the recess of the chamber such that the plurality of light emitting diodes provide ultraviolet light towards the recess.

In accordance with another embodiment of the present disclosure, there is provided a dental hygiene device including a housing, a toothbrush, and a sanitizing device. The housing includes a base portion and a cover hingedly coupled to the base portion to transition between open and closed positions. The toothbrush is selectably coupled with housing. The toothbrush includes a head portion including bristles and an engaging portion. The toothbrush is reconfigurable with the housing between a first configuration, in which the bristles are external of the housing and a second configuration, in which, the bristles are disposed within the housing. The sanitizing device includes a plurality of light emitting diodes to provide ultraviolet light to the bristles when the toothbrush is in the second configuration.

In an embodiment, the housing may include a tapered profile. In another embodiment, the housing may include scalloped portions.

In another embodiment, the housing may define a chamber including a reflective surface. In particular, the reflective surface may include at least one of a polyester film, a metallic foil, or a reflective coating.

In yet another embodiment, the housing may define a recess in registration with the bristles when the toothbrush is in the second configuration.

In another embodiment, the base portion may include a storage compartment configured to receive an oral care material.

In yet another embodiment, the base portion may include a cover panel configured to detachably enclose the storage compartment.

In still yet another embodiment, the cover panel may be configured to detachably engage the base portion by friction fit or snap fit.

BRIEF DESCRIPTION OF THE DRAWINGS

The above and other aspects and features of the present disclosure will become more apparent in light of the following detailed description when taken in conjunction with the accompanying drawings in which.

DETAILED DESCRIPTION

Particular embodiments of the present disclosure will be described herein with reference to the accompanying drawings. As shown in the drawings and as described throughout the following description, and as is traditional when referring to relative positioning on an object, the terms "proximal" and "trailing" may be employed interchangeably, and should be understood as referring to the portion of a structure that is closer to a clinician during proper use. The terms "distal" and "leading" may also be employed interchangeably, and should be understood as referring to the portion of a structure that is farther from the clinician during use as will be described hereinbelow. In the following description, well-known functions or constructions are not described in detail to avoid obscuring the present disclosure in unnecessary detail.

With reference to FIGS. 1-4, an embodiment of the present disclosure is shown generally as a dental hygiene device 100. Dental hygiene device 100 includes a housing 10, a toothbrush 50 reversibly attachable to housing 10, and a sanitizing device 80 configured to sterilize portions of toothbrush 50 disposed within housing 10. Toothbrush 50 and sanitizing device 80 are selectively mountable with housing 10 such that toothbrush 50 and sanitizing device 80 may be utilized independent of each other. It is also envisioned that housing 10 and sanitizing device 80 can be employed to sterilize conventional toothbrushes.

Figure 1:
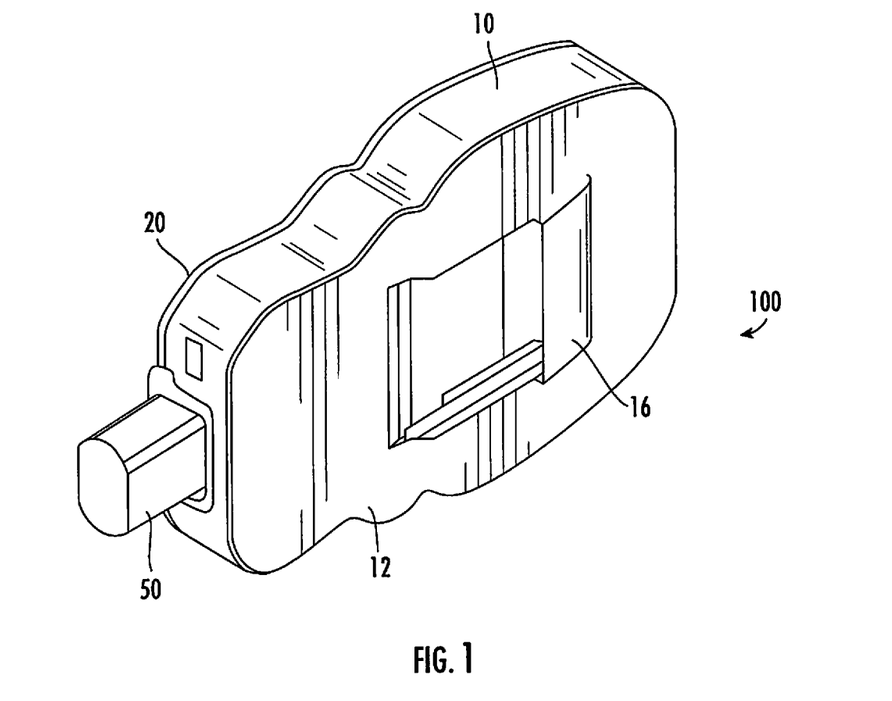
FIG. 1 is a bottom perspective view of a dental hygiene device in accordance with an embodiment of the present disclosure.
Figure 2:
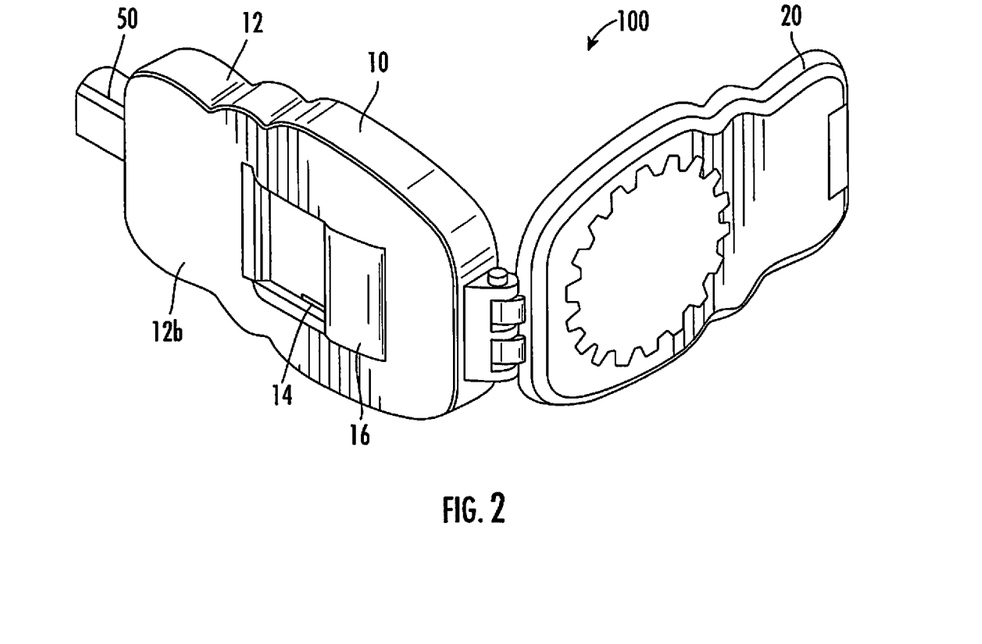
FIG. 2 is a bottom perspective view of the dental hygiene device of FIG. 1, illustrating opening of a cover of a housing of the dental hygiene device.
Figure 3:
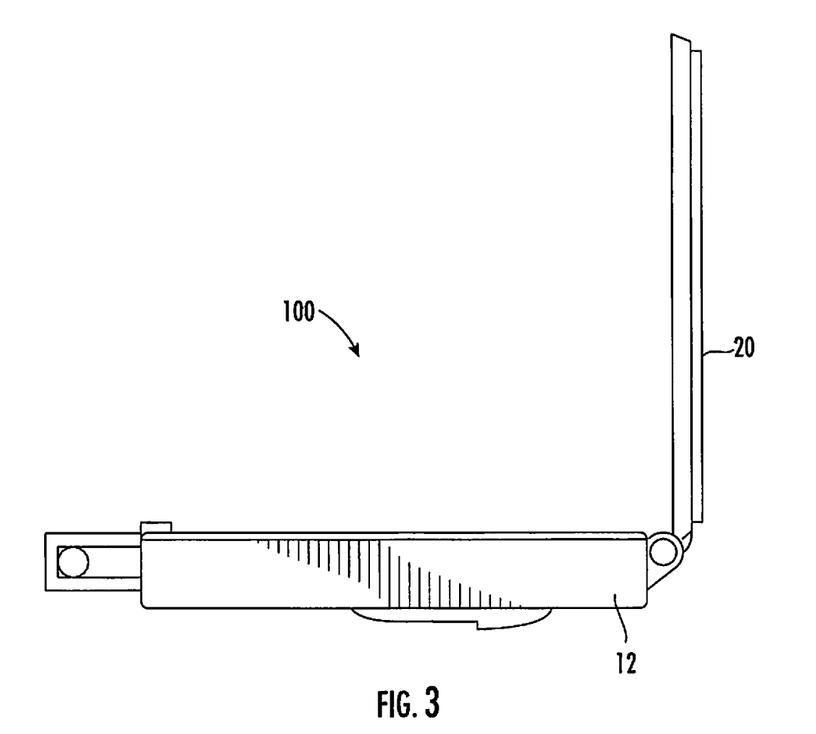
FIG. 3 is a side view of the dental hygiene device of FIG. 2.
Figure 4:
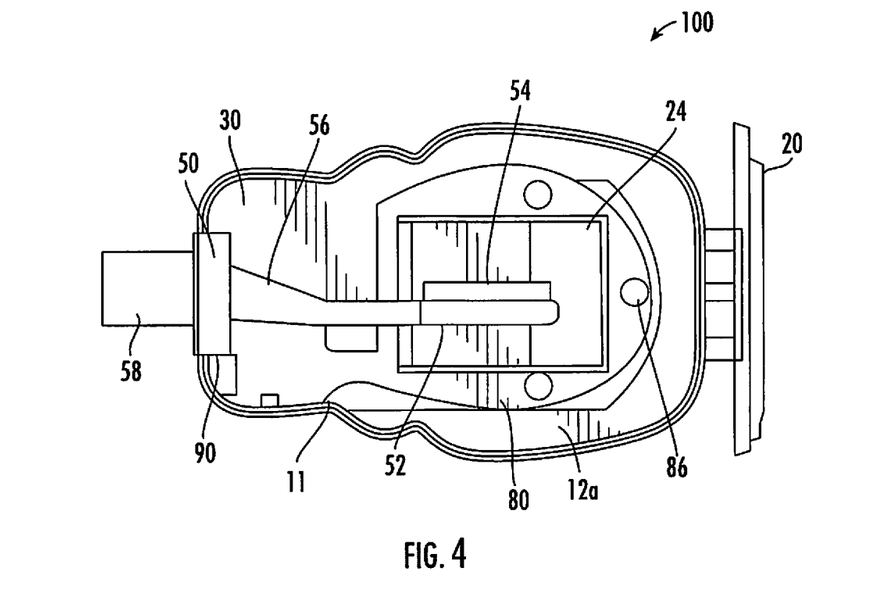
FIG. 4 is a top view of the dental hygiene device of FIG. 2.

With particular reference to FIGS. 2-4, housing 10 includes a base portion 12 and a cover 20 hingedly coupled to base portion 12. Cover 20 is transitionable between an open position, in which, a chamber 30 of housing 10 is accessible to load or unload toothbrush 50 and sanitizing device 80 into and out of chamber 30, and a closed position, in which cover 20 is closed to contain ultraviolet (UV) light in chamber 30 during a sterilization cycle or for storage of toothbrush 50 in chamber 30. A clasp, friction fit, or other component may be provided for securing cover 20 in the closed position. In the closed position, cover 20 may engage base portion 12 in a sealing relation.

Figure 5:
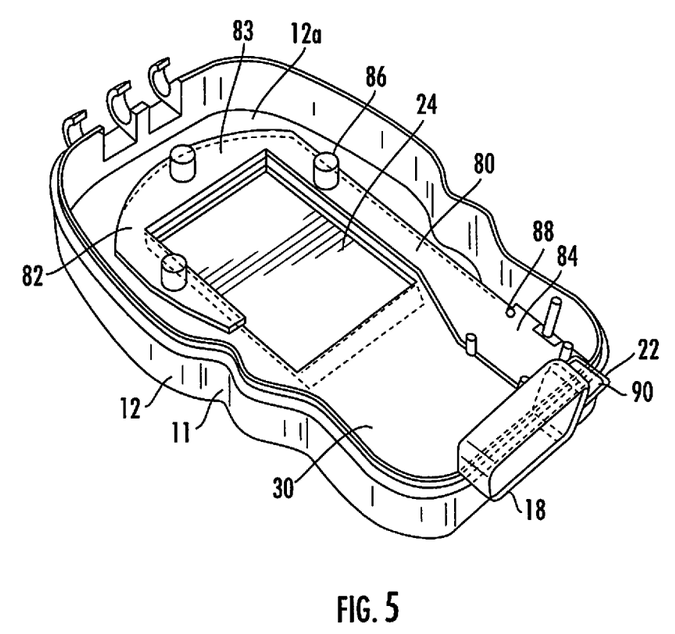
FIG. 5 is a top perspective view of a base portion of the housing of FIG. 1.
Figure 6:
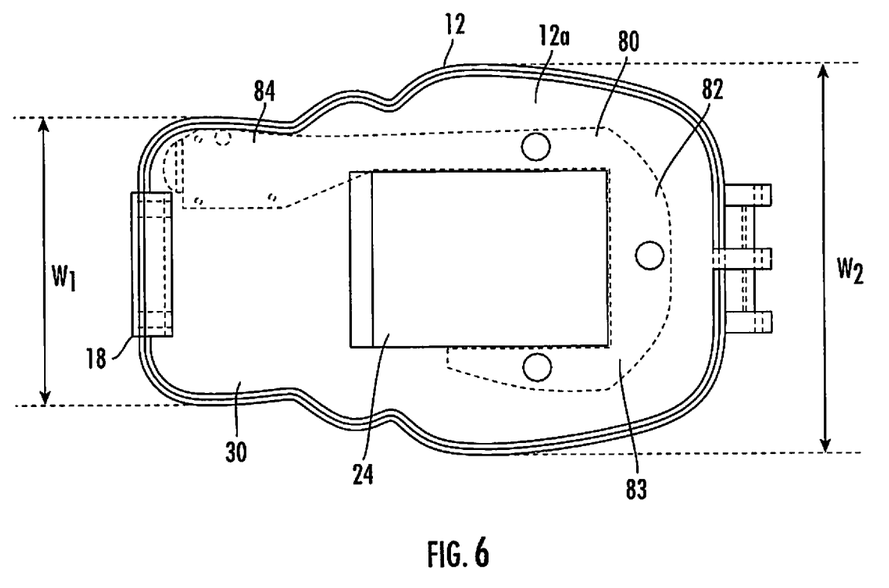
FIG. 6 is a top view of the base portion of FIG. 5, illustrating the sanitizing device in phantom.

With reference to FIGS. 4-6, base portion 12 further defines a mouth 18 configured to secure a portion of toothbrush 50 therein and an opening 22 in registration with a USB port 90 of sanitizing device 80, as will be discussed. Housing 10 may include a first width $W_1$ adjacent mouth 18 and a second width $W_2$ spaced apart from mouth 18. Second width $W_2$ may be larger than $W_1$ to facilitate gripping by a user. Housing 10 may include scalloped portions 11 to further facilitate gripping of housing 10 by the user. However, it is further contemplated that housing 10 may include other ergonomic and/or friction enhancing elements to facilitate gripping. Examples of such elements may include protuberances, knurling, elastomeric material, or any combination thereof. Under such a configuration, toothbrush 50 may be selectively reconfigurable with housing 10 such that housing 10 is utilized as a handle, with an enlarged grip for conventional operation of toothbrush 50.

With brief reference back to FIG. 4, toothbrush 50 is reversibly engageable with housing 10. In particular, toothbrush 50 includes a head portion 52 including bristles 54, a neck portion 56 extending from head portion 52, and an engaging portion 58 configured to be removably attached to mouth 18 of base portion 12 by, e.g., friction fit or snap fit configuration, to enable reversible attachment of toothbrush 50 to base portion 12. Under such a configuration, engaging portion 58 of toothbrush 50 engages mouth 18 (FIG. 5) to securely retain head portion 52 within chamber 30 for storage or sterilization or to enable head portion 52 to extend out of housing 10 such that housing 10 is utilized as a handle with an enlarged grip for conventional operation of toothbrush 50. Engaging portion 58 of toothbrush 50 may engage mouth 18 in a sealing relation.

With reference to FIGS. 4-6, base portion 12 includes an inner portion 12a and an outer portion 12b (FIG. 2). Inner portion 12a includes chamber 30 configured to selectively receive toothbrush 50 and sanitizing device 80 therein. Chamber 30 includes a reflective interior surface. The sterilization of toothbrush 50 is enhanced by coating or otherwise forming the interior surface of chamber 30 with a reflective material. The reflective surface enables vectoring of the UV light generated by light emitting diodes (LEDs) 86 towards bristles 54 of head portion 52 of toothbrush 50 when bristles 54 are in chamber 30. The reflective interior surface may include a polyester film, a metallic foil, a reflective coating, or other reflective material sufficient to reflect UV light about an interior volume of chamber 30.

Inner portion 12a of base portion 12 further defines a recess 24 such that when toothbrush 50 is received in chamber 30, bristles 54 of toothbrush 50 are spaced apart from an interior surface of chamber 30 for, e.g., faster drying of bristles 54 and/or enhanced effectiveness of sterilization of bristles 54.

With brief reference back to FIG. 2, outer portion 12b defines a recess 14 configured to receive an oral care material (not shown) such as, e.g., a breath freshener strips, and includes a rim 16 configured to retain the oral care material in recess 14.

Figure 7:
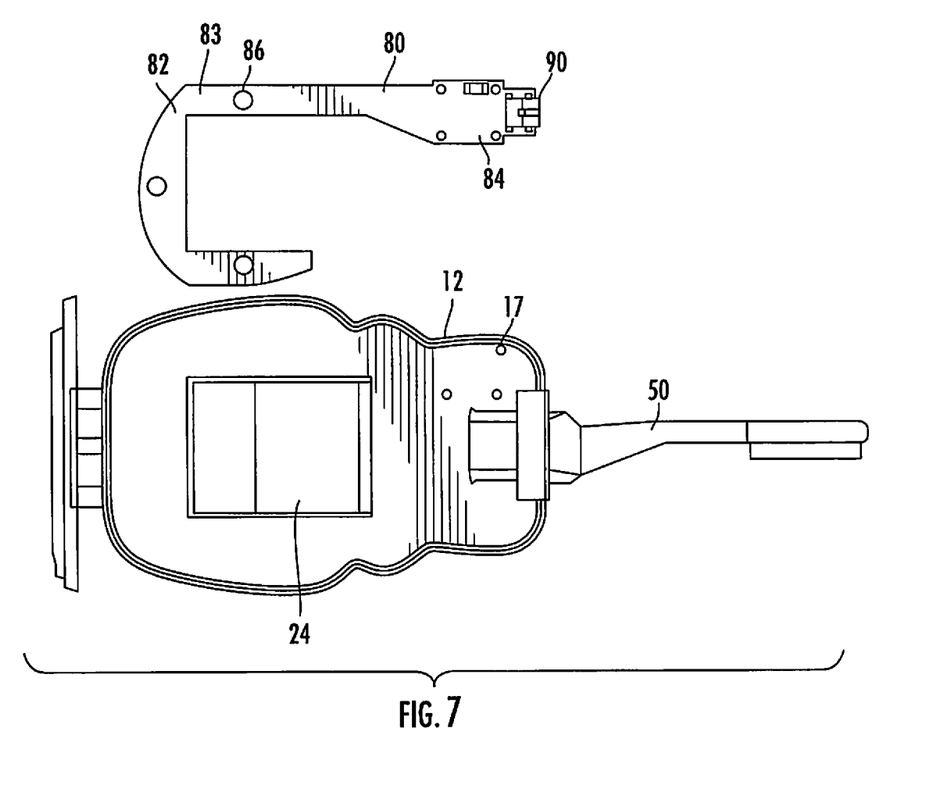
FIG. 7 is a top view of the dental hygiene device of FIG. 1, illustrating reconfiguration of a toothbrush and a sanitizing device separated from the housing.

With reference to FIGS. 5-7, chamber 30 of housing 10 is configured to detachably receive sanitizing device 80 therein. Sanitizing device 80 includes a circuit board 82. Circuit board 82 includes a first portion 83 at least partially surrounding recess 24, and a second portion 84 configured to be mounted to base portion 12. First portion 83 includes a means for UV radiation positioned to direct UV light towards recess 24. For example, first portion 83 may include a plurality of LEDs 86 generating UV light in the range of about 100-280 nm. Power may be supplied to LEDs 86 through the use of standard interfaces, such as, e.g., a Universal Serial Bus (USB). First portion 83 may be, e.g., hook shaped. However, other shapes and configurations may be used to direct UV light towards recess 24 and to enable the UV light to be reflected at multiple angles to allow penetration to all areas of bristles 54 of toothbrush 50.

Second portion 84 includes a plurality of pins 88 configured to engage a plurality of bores 17 defined in inner portion 12a of base portion 12 in order to detachably secure sanitizing device 80 to base portion 12. Second portion 84 further includes USB port 90 mounted thereon. USB port 90 is in registration with opening 22 of base portion 12. The plurality of LEDs 86 is electrically coupled with USB port 90. USB port 90 may be connected to a power source, e.g., a computer, to supply power to LEDs 86. It is further contemplated that USB port 90 may engage opening 22 of base portion 12 by, e.g., friction fit or snap fit configuration, to secure sanitizing device 80 with base portion 12, thereby eliminating the need for pins 88.

Figure 8:
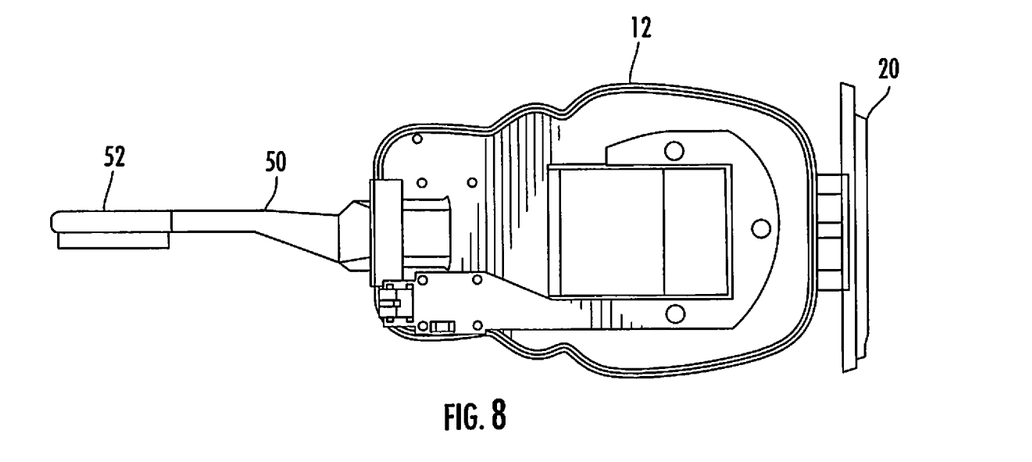
FIG. 8 is a top view of the dental hygiene device of FIG. 7.
Figure 9:
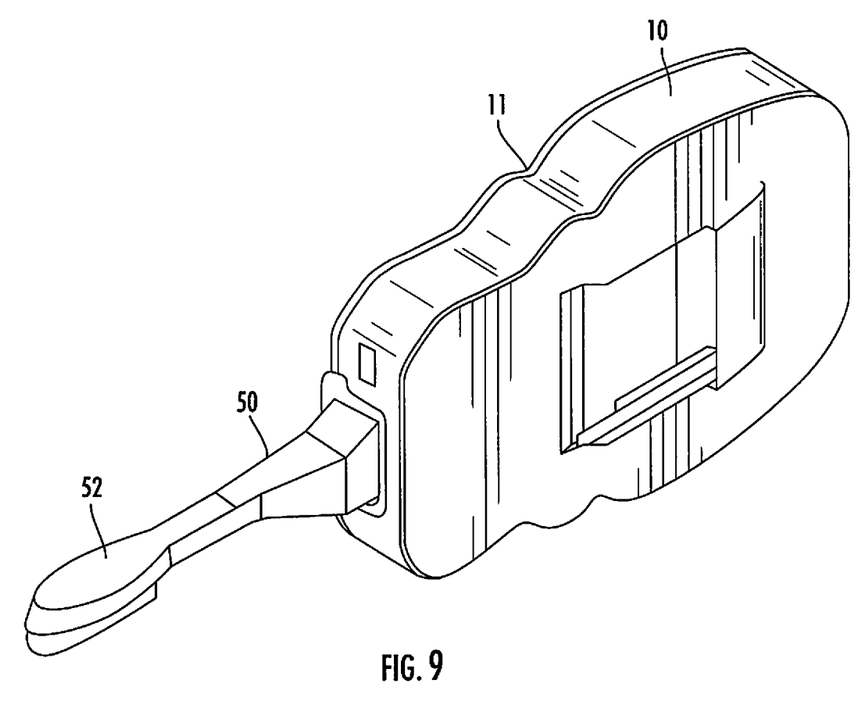
FIG. 9 is a perspective view of the dental hygiene device of FIG. 8, illustrating the toothbrush in a configuration for use.
Figure 10:
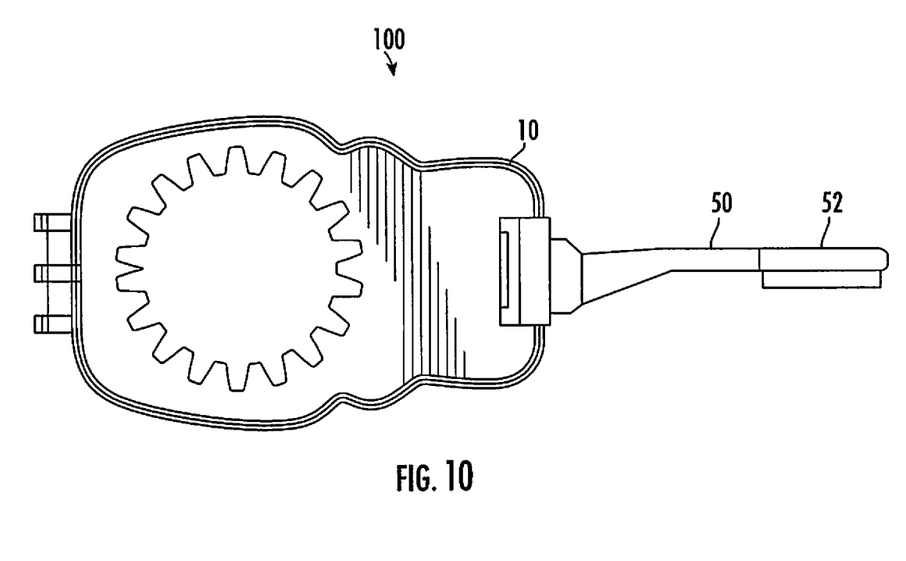
FIG. 10 is a top view of the dental hygiene device of FIG. 9.
Figure 11:
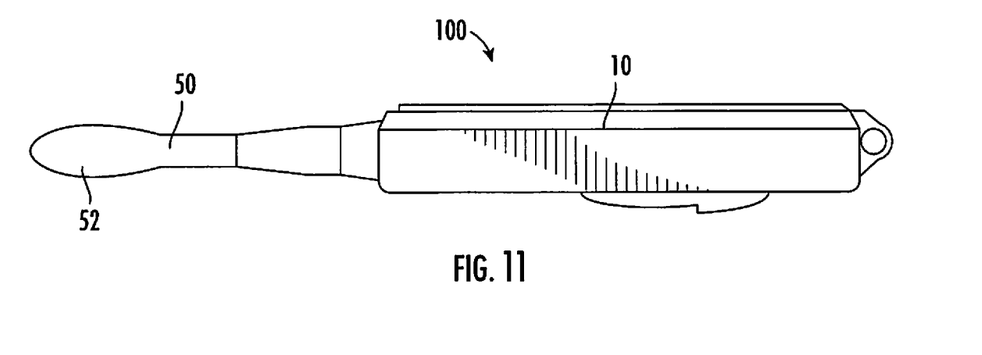
FIG. 11 is a side view of the dental hygiene device of FIG. 10.

Initially, toothbrush 50 is reversibly attached to housing 10 such that bristles 54 are disposed in chamber 30, and sanitizing device 80 is mounted in chamber 30. USB port 90 may be connected to, e.g., a computer, to supply power to LEDs 86 to sterilize bristles 54 prior to use. With reference to FIG. 8, upon completion of sterilizing bristles 54, engaging portion 58 may be detached from housing 10 and reattached thereto such that head portion 52 is external of housing 10. In this manner, toothbrush 50 may be secured to housing 10 to utilize housing 10 as a handle for toothbrush 50, as shown in FIGS. 9-11. At this time, sanitizing device 80 may be optionally removed from chamber 30 prior to using toothbrush 50. After use, toothbrush 50 may be reconfigured to place bristles 54 in chamber 30 for storage and/or sterilization. While dental hygiene device 100 is shown to be used with toothbrush 50, it is also envisioned that dental hygiene device 100 may be utilized to sterilize other dental devices, such as, e.g., retainers.

Figure 12:
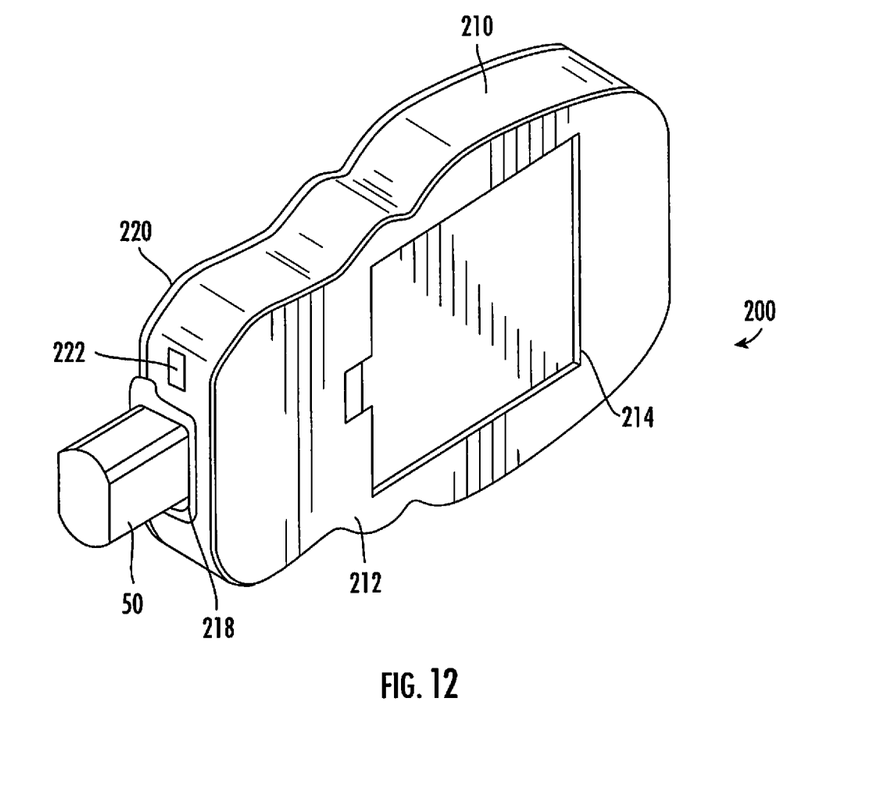
FIG. 12 is a bottom perspective view of a dental hygiene device in accordance with another embodiment of the present disclosure.
Figure 13:
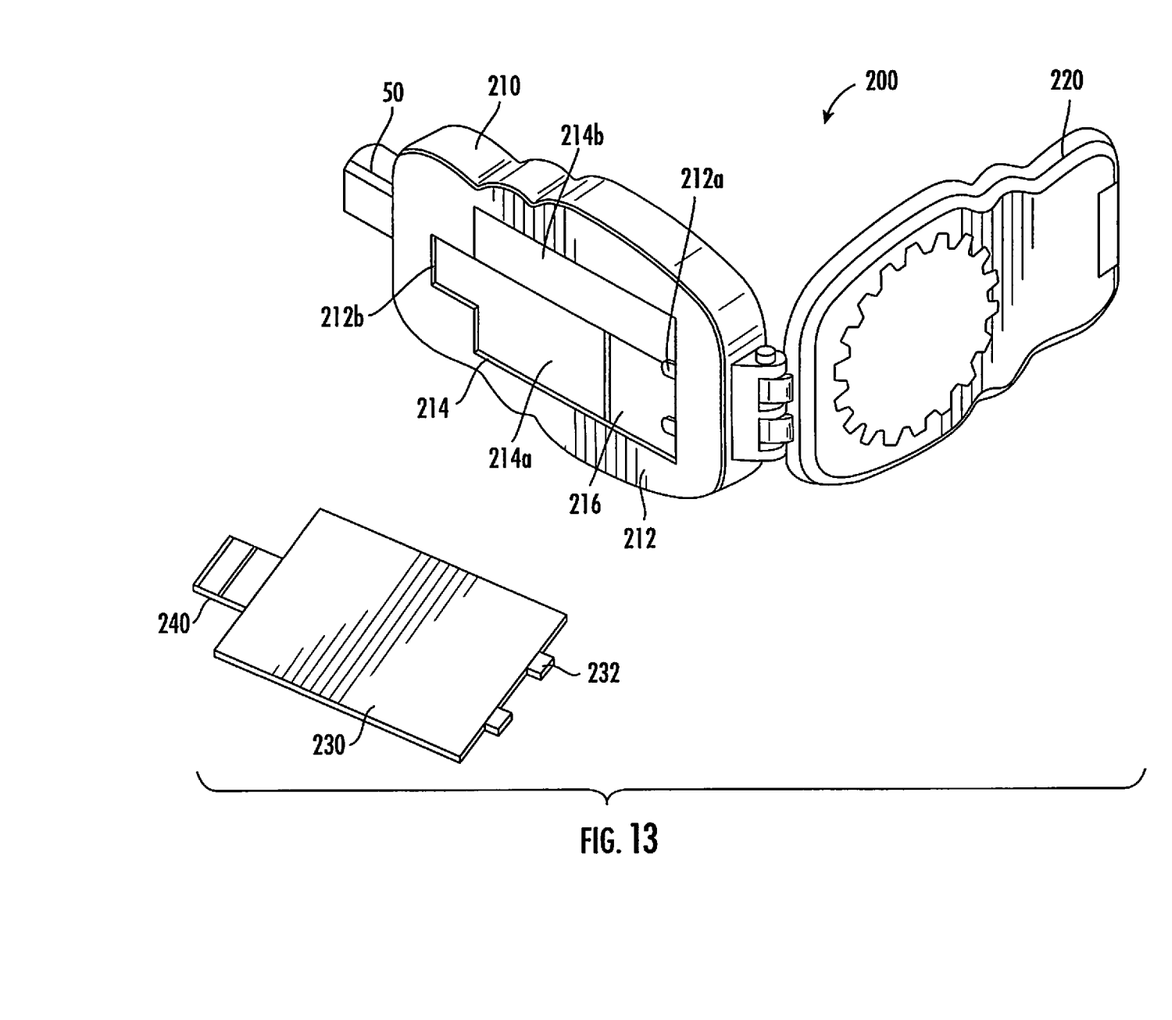
FIG. 13 is a bottom perspective view of the dental hygiene device of FIG. 12, illustrating a storage compartment with a cover panel separated.

With reference to FIGS. 12 and 13, there is illustrated a dental hygiene device 200 in accordance with another embodiment of the present disclosure. Dental hygiene device 200 includes features that are identical to the features described with respect to dental hygiene device 100. Thus, the identical parts in dental hygiene device 200 will not be described herein to avoid obscuring the present disclosure in unnecessary detail.

Dental hygiene device 200 includes a housing 210, toothbrush 50 reversibly attachable to housing 210, and sanitizing device 80 (FIG. 4) configured to sterilize portions of toothbrush 50 disposed within housing 210. Toothbrush 50 and sanitizing device 80 are selectively mountable with housing 210 such that toothbrush 50 and sanitizing device 80 may be utilized independent of each other.

Housing 210 includes a base portion 212 including a storage compartment 214 configured to receive an oral care material (not shown), and a cover 220 hingedly coupled to base portion 212. Cover 220 is transitionable between an open position, in which, a chamber of housing 210 is accessible to load or unload toothbrush 50 and sanitizing device 80 into and out of the chamber, and a closed position, in which cover 220 is closed to contain ultraviolet (UV) light in the chamber during a sterilization cycle or for storage of toothbrush 50 in the chamber. Base portion 212 and cover 220 may be configured to provide a reset switch that controls supply of power to LEDs 86, when cover 220 transitions between the open and closed positions. As discussed hereinabove, USB port 90 may be connected to a power source, e.g., a computer, to directly supply power to LEDs 86. Depending on the circuit board being used, a battery (not shown) may be provided in housing 210. In addition, a safety switch (not shown) may be further provided to manually control supply of power to LEDs 86.

Base portion 212 of housing 210 further defines a mouth 218 configured to secure a portion of toothbrush 50 therein and an opening 222 in registration with USB port 90 (FIG. 5) of sanitizing device 80. Toothbrush 50 may be selectively reconfigurable with housing 210 such that housing 210 is utilized as a handle, with an enlarged grip for conventional operation of toothbrush 50.

Base portion 212 includes storage compartment 214. Storage compartment 214 includes a first portion 214a configured to receive, e.g., a breath freshener strips (not shown). First portion 214a may include a rim 216 configured to retain the oral care material in first portion 214a. Storage compartment 214 further includes a second portion 214b defining, e.g., a groove, configured to receive, e.g., a tube of toothpaste (not shown). Base portion 212 further includes a cover panel 230 configured to detachably enclose storage compartment 214. Cover panel 230 includes guiding tabs 232 configured to be received in respective grooves 212a defined in base portion 212 to facilitate alignment of cover panel 230 with base portion 212. Cover panel 230 further includes a neck portion 240 dimensioned to engage a securing portion 212b of base portion 212. Cover panel 230 may be detachably coupled with base portion 212 by, e.g., friction fit or snap fit configuration. In this manner, a user may access storage compartment 214 independent of open cover 220. The use of dental hygiene device 200 is similar to that of dental hygiene device 100 described hereinabove, and thus will not be described herein. It is also envisioned that the oral care material such as, e.g., the toothpaste and the breath freshener strips, may be provided as a module that can be attached to storage compartment 214 without cover panel 230. It is contemplated that base portion 212 may be 3D printed as a circuit board. For example, non-conductive filament may be used for housing 10, and conductive filament may be embedded for circuit. In addition, reflective filament may be used for light dispersement.

Although the illustrative embodiments of the present disclosure have been described herein with reference to the accompanying drawings, the above description, disclosure, and figures should not be construed as limiting, but merely as exemplifications of particular embodiments. For example, dental hygiene device 100 may be powered by a single power source, such as disposable batteries, rechargeable batteries, or other commercially available power source. It is further contemplated that a wave tone generator may be utilized with or without sanitizing device 80 for ultrasonic or sound sterilization. It is to be understood, therefore, that the disclosure is not limited to those precise embodiments, and that various other changes and modifications may be effected therein by one skilled in the art without departing from the scope or spirit of the disclosure.

What is claimed is:
1. A dental hygiene device comprising:
 a housing including a base portion and a cover hingedly coupled to the base portion to transition between open and closed positions, the housing defining a recess and an opening in communication with an interior and an exterior of the housing;
 a sanitizing device including a hook portion having a plurality of light emitting diodes configured to provide ultraviolet light, the hook portion disposed in the base portion and partially extending around a periphery of the recess; and
 a toothbrush selectably coupled with housing, the toothbrush including a head portion including bristles, and an engaging portion, the toothbrush reconfigurable with the housing between a first configuration, in which, the bristles are external of the housing and a second configuration, in which, the bristles are in registration with the recess of the housing.

2. The dental hygiene device according to claim 1, wherein the housing defines a chamber including a reflective surface including at least one of a polyester film, a metallic foil, or a reflective coating.

3. The dental hygiene device according to claim 1, wherein the housing includes a tapered profile, the housing including scalloped portions.

4. The dental hygiene device according to claim 3, wherein the scalloped portions of the housing facilitate gripping by a user.

5. The dental hygiene device according to claim 1, wherein the opening of the housing is configured to selectively support the hook portion.

6. The dental hygiene device according to claim 1, wherein the base portion includes a storage compartment configured to receive an oral care material.

7. The dental hygiene device according to claim 6, wherein the base portion includes a cover panel configured to detachably enclose the storage compartment.

8. The dental hygiene device according to claim 7, wherein the cover panel is configured to detachably engage the storage compartment by friction fit or snap fit.

9. A dental hygiene device comprising:
a housing including a chamber therein, the housing defining a mouth and an opening in communication with the chamber and an exterior of the housing, the housing including a first width adjacent the mouth and a second width spaced apart from the mouth, the second width larger than the first width;
a sanitizing device attachable to the housing and positionable in the chamber, the sanitizing device having a hook that partially extends around a periphery of a recess of the chamber, the hook configured to provide ultraviolet light; and
a toothbrush detachably securable with the mouth of the housing, the toothbrush including a head portion including bristles, and an engaging portion, the toothbrush reconfigurable with the housing between a first configuration, in which, the bristles are external of the housing, and a second configuration, in which, the bristles are disposed within the chamber.

10. The dental hygiene device according to claim 9, wherein the housing includes a base portion and a cover hingedly coupled to the base portion.

11. The dental hygiene device according to claim 9, wherein the base portion includes an outer surface defining the recess that is configured to receive an oral care material.

12. The dental hygiene device according to claim 9, wherein the housing includes scalloped portions.

13. The dental hygiene device according to claim 12, wherein the scalloped portions of the housing facilitate gripping by a user.

14. The dental hygiene device according to claim 9, wherein the mouth is adjacent the opening.

15. The dental hygiene device according to claim 9, wherein the chamber includes a reflective surface.

16. The dental hygiene device according to claim 9, wherein the housing is configured to detachably support the engaging portion of the toothbrush.

* * * * *